United States Patent [19]

Hoffmaster

[11] Patent Number: 4,549,807

[45] Date of Patent: Oct. 29, 1985

[54] PROCESS FOR MEASURING FLUORESCENCE

[75] Inventor: Timothy D. Hoffmaster, Toms River, N.J.

[73] Assignee: AT&T Bell Laboratories, Murray Hill, N.J.

[21] Appl. No.: 539,793

[22] Filed: Oct. 7, 1983

[51] Int. Cl.⁴ .............................................. G01N 21/64
[52] U.S. Cl. ................................ 356/318; 250/459.1; 436/172
[58] Field of Search ............... 356/301, 317, 318, 417; 250/365, 372, 373, 458.1, 459.1, 461.1, 461.2; 436/172

[56] References Cited

U.S. PATENT DOCUMENTS

| | | | |
|---|---|---|---|
| 3,612,866 | 10/1971 | Stevens | 250/373 |
| 3,725,658 | 4/1973 | Stanley et al. | 250/364 |
| 4,272,248 | 6/1981 | Neti | 436/172 X |
| 4,394,237 | 7/1983 | Donnelly et al. | 204/192 R |

*Primary Examiner*—F. L. Evans
*Attorney, Agent, or Firm*—Bruce S. Schneider

[57] ABSTRACT

Fluorescent measurements are taken utilizing a Raman enhancing surface by a method which allows reduction or essentially complete elimination of interference by fluorescence quenchers. In particular, the fluorescent medium to be measured is interacted with a Raman enhancing surface. Through this interaction between the Raman enhancing surface and the fluorescing species, fluorescence quenching is eliminated. The quenching is particularly significant in analytical procedures such as those involved in chromatography and medical testing.

7 Claims, 3 Drawing Figures

PROCESS FOR MEASURING FLUORESCENCE

BACKGROUND OF THE INVENTION

1. Field of the Invention

This invention relates to spectroscopic measurements and, in particular, spectroscopic measurements involving emission.

2. Art Background

Spectroscopic measurements are utilized in a host of analytical techniques. For example, such measurements are often utilized to detect the presence of various spectroscopically active biological species. Spectroscopic measurements are also utilized, in another common application, to detect the presence of various sample components exiting a chromatographic column. Generally, in analytical spectroscopic techniques, irrespective of the particular application, the presence of a specific chemical species is detected through the interaction of electromagnetic radiation with the species. The most commonly employed spectroscopic methods are absorption techniques—monitoring of absorbed electromagnetic radiation—and fluorescent techniques—the monitoring of emitted radiation including but not limited to fluorescence and phosphorescence. Although absorption techniques are quite useful, generally fluorescence measurements are significantly more sensitive. Thus, the utilization of fluorescence techniques potentially allows the detection of a greater variety of chemical entities at lower concentrations.

In fluorescence techniques the entity to be detected is excited utilizing incident electromagnetic radiation. Upon relaxation of this excitation, light is emitted that is indicative of the species being monitored. Although fluorescence measurements offer the possibility of greater sensitivity, quenching of emission from a potentially fluorescing species by interaction with a second entity often significantly diminishes or eliminates this advantage. Although some quenching is induced by interaction of a solid sample with its gaseous environment, i.e., air, this interaction resulting, for example, from adsorption of gas, e.g., oxygen, on the solid sample surface is easily eliminated by operating in a non-quenching inert atmosphere, e.g., making the measurement under nitrogen or helium. The most significant quenching processes, however, involve the interaction of a quenching entity with the excited species in a condensed phase. (A condensed phase for purposes of this disclosure is a solid or a phase whose density is no less than 50 percent of the density measured for the same composition in the solid phase. Interaction refers to effects produced by the presence of one entity in the vicinity of another where these two entities are not the specific combination of a solid and a gas absorbed directly from a gaseous environment onto the surface of the solid.) The quenching in these significant systems occurs through various interactions—in solids, for example, by contact with a quencher from a source other than by direct adsorption from a gaseous environment and in other condensed phases by, for example, contact with the quencher, e.g., through dissolution in a solution containing the fluorescing species. In one specific example, although rhodamine B fluoresces intensely upon excitation with blue-green light, the presence of iron quenches this emission by conversion to a non-radiative state. This undesirable quenching is often caused by reagents typically utilized in analytical techniques or in the case of biological investigations by chemical species typically present in biological systems. Thus, for many significant applications, although sensitive measurements are quite desirable, the additional sensitivity provided by fluorescence measurements is not available and absorption techniques are being employed.

SUMMARY OF THE INVENTION

The quenching of fluorescence in condensed phases is substantially reduced or eliminated in analytical measurements through the use of Raman enhancing surfaces. This phenomenon extends essentially to all significant quenching systems. In particular, a metal surface that is capable of supporting plasmons and is further capable of yielding enhanced Raman spectra is utilized. The fluorescing composition is induced to interact with this enhancing surface by conventional techniques. For example, a solution is deposited on the surface and the solvent removed through spinning. By choosing an enhancing medium whose plasmon frequency suitably matches spectral properties of the fluorescing species, the lifetime for fluorescence is substantially reduced, i.e., reduced by a factor of at least three. Through this substantially shortened fluorescence time the opportunity for competing process such as quenching is substantially reduced or essentially eliminated. Thus, fluorescence is detectable in circumstances where, due to the presence of a quenching species, only non-measurable levels of fluorescence were previously obtained.

DETAILED DESCRIPTION

Figure 2:
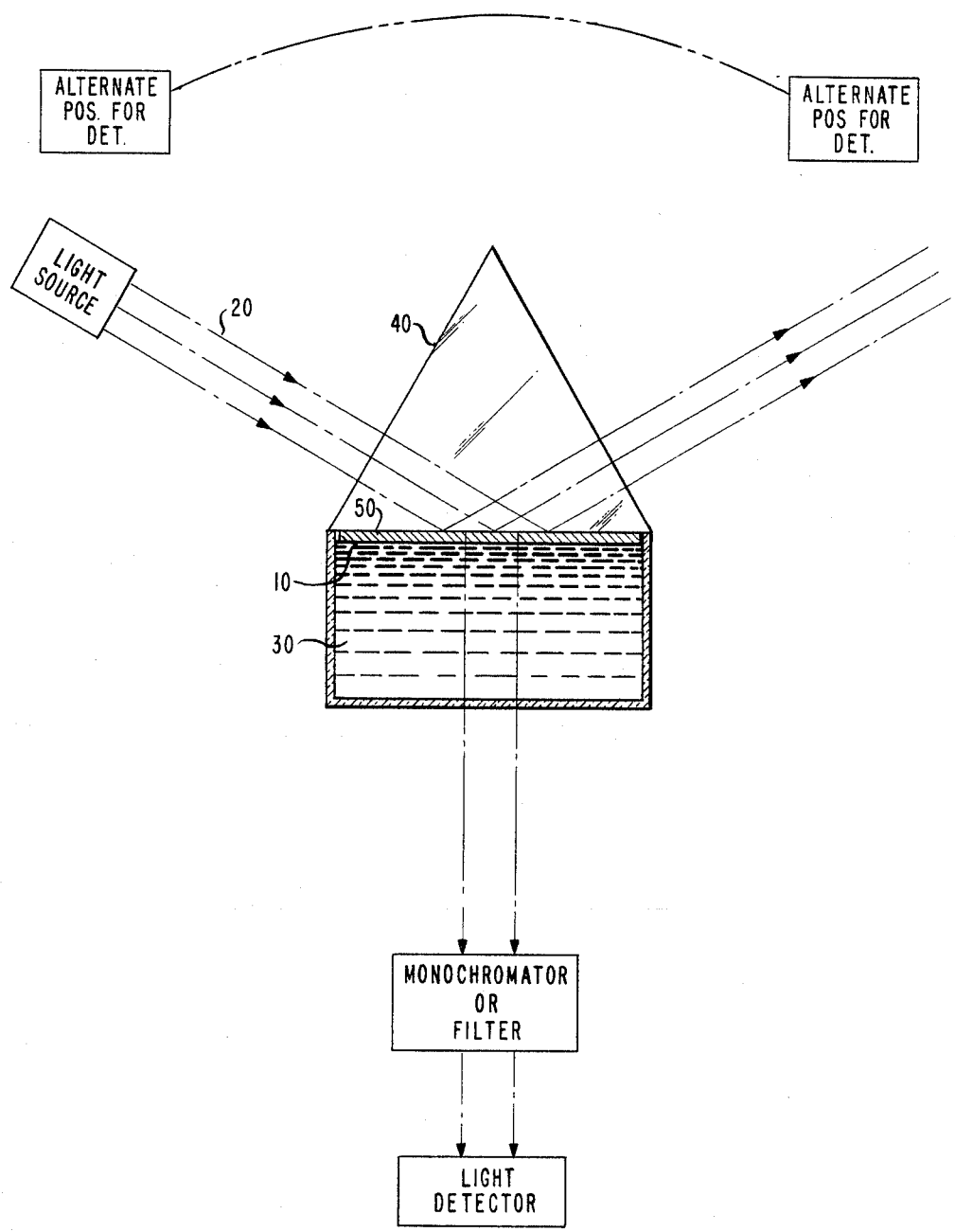

The substantial reduction of quenching in fluorescence measurements is achieved through the interaction of plasmons generated in Raman enhancing surfaces, e.g., metal particle surfaces, with the excited spectroscopic state of the fluorescing molecule. The particular composition and configuration of the enhancing surface utilized should be chosen to correspond to the particular fluorescence spectrum to be observed. This matching of plasmon and excited fluorescing state is easily accomplished. To determine if an enhancing surface is a suitable match for the fluorescing species, the enhancing surface to be employed in the analytical measurements (typically a particulate metal surface) is treated with a material (not necessarily the one that is ultimately to be investigated) that has a Raman active vibrational mode. The treatment scheme for this determination is not critical. For example, in one scheme a solution of the molecule is deposited on the roughened surface and the solvent is removed through spinning. Alternatively in a second scheme, the enhancing surface is formed on a prism as indicated in FIG. 2. The surface, 10, is then contacted with a solution of the molecule, 30, and light excitation, 20, is introduced through the prism, 40, to the enhancing surface. A Raman spectrum, as described in *Laser Raman Spectroscopy*, (New York: Wiley Interscience, 1970), of the treated enhancing surface is then taken by conventional techniques over the frequency range associated with the fluorescence to be observed. (This frequency range is that corresponding to the emission region to be ultimately monitored for the fluorescing state of the composition to be detected in an environment where there is no interaction with a Raman enhancing surface.) In one exemplary embodiment a convenient moiety, e.g., a cyanide moiety is introduced onto the particle array. This introduction is performed, for example, by exposure to HCN as described in Liao, et al, *Chemical Physics Letters*, 82, 355, (1981). A Raman excitation spectrum is then determined by varying the excitation wavelength onto the enhancing surface and detecting scattered light over a wavelength range varying at the same rate as the excitation wavelength while maintaining a constant energy difference between the excitation wavelength and detection wavelength. (An energy difference between 500 to 3000 cm$^{-1}$ are typically employed.) For a suitable match, irrespective of the chosen Raman active species, the integrated intensity of the Raman measurement in the appropriate spectral range should be at least 100 times, preferably 1000 times, that of the Raman spectrum observed in the absence of the enhancing surface. Through the satisfication of the matching criterion the fluorescence lifetime is shortened by a factor of at least 3, generally at least 5, and up to approximately 10,000. Thus, the rate of quenching phenomenon relative to the fluorescence rate becomes either substantially less significant or essentially negligible.

Suitable materials for forming surfaces that satisfy the matching criterion are those within the frequency range of the emission to be monitored having the real part of their dielectric constant in the range $-1.5$ to $-2.5$. (Compilations of refractive indices from which the dielectric constant is easily calculated, as discussed by Hass and Hadley, "Optical Properties of Metals," *American Institute of Physics Handbook*, 3rd ed., (New York: McGraw Hill), for a wide variety of metals are compiled in texts such as found in the *American Institute of Physics Handbook, supra.*) The chosen material is then formed into a surface configuration that produces Raman enhancement, e.g., a surface having at least 1 percent of its area with a radius of curvature whose absolute value is smaller than the average wavelength of the light to be monitored. For example, a Raman enhancing particulate surface is produced by depositing a metal on a surface which it does not wet. (See, for example, Weitz, et al, *Journal of Chemical Physics*, 78(9), 5324, (1983).) Alternatively, a regular array of disjoint regions, e.g., metal regions, is produced by standard lithographic techniques such as disclosed in Liao, supra. Enhancing surfaces are also producible by electrochemical processes such as described by R. P. van Duyne, *Chemical and Biochemical Applications of Lasers*, 14, ed. C. B. Moore (New York: Academic Press, 1978). A controlled sample is utilized to determine the most advantageous configuration for a chosen material and for the particular fluorescing species that is to be monitored.

The light source utilized to induce fluorescence in the inventive spectroscopic determination is not critical. Generally, either coherent light such as that produced by lasers or incoherent light such as that produced by lamps, e.g., xenon lamps, is employable. Typically, the power levels useful for yielding an easily detectable level of fluorescence is at least $10\mu$ watts at wavelengths at which the absorption of the sample is at least 10 percent of the peak absorption for that sample. It is generally advantageous that the intensity of the light of the excitation source, however, be limited so that it does not cause dissociation of the species to be monitored. Typically, light sources having powers less than 1 watt/cm$^2$ avoid possible dissociations.

Typical materials utilized for forming an enhancing surface are silver, gold, and copper. These metals have plasmon frequency in the range between 400 and 600 nm. Generally, this specific range is useful for analytical measurements. The substrate (if one is employed) on which the particle array is formed is not critical. However, if wetting interactions between the enhancing composition and the substrate are utilized to produce the Raman enhancing surface, the substrate material should be chosen to yield a suitable surface configuration.

The intensity of fluorescence and the degree of quenching varies with the distance of the fluorescing species from the specific enhancing surface. Each specific variation depends individually on the particular species being monitored and on the specific enhancing surface. Generally, the average spacing of the fluorescing species measured to the closest point on the Raman enhancing surface should be less than 2 times the average of the absolute values for the radii of curvature of the portions of the interacting Raman enhancing surface that satisfy the less than-the-average-wavelength curvature criterion previously discussed. The average spacing is controlled by a conventional expedient such as coating the enhancing surface with an intermediary material that is a non-conductor—a material having a resistivity greater than $10^{-2}$ ohm-cm. (A zero average spacing, i.e., no intermediary layer is also employable.) Exemplary of intermediary materials are polymers such as poly(methyl methacrylate) that are coated by conventional techniques such as spinning. A control sample is employed to yield a suitable fluorescence intensity with the desired level of quenching.

Figure 1:
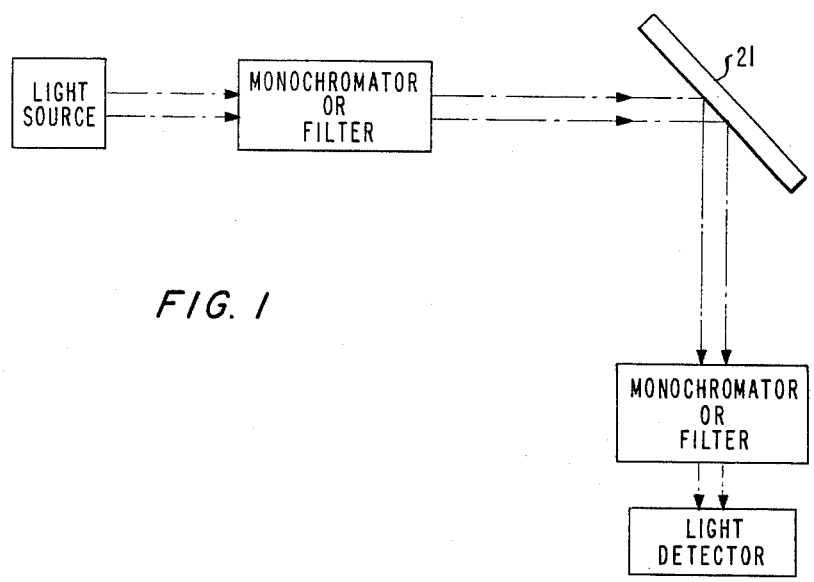
FIG. 1 is illustrative of an apparatus suitable for the practice of the invention.
Figure 3:
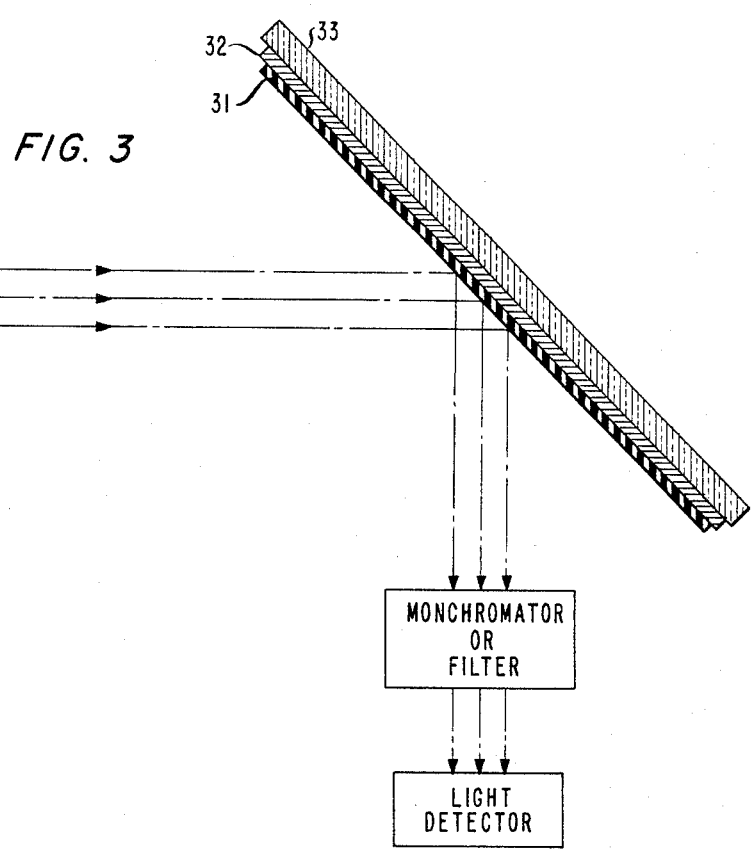
FIGS. 2 and 3 are illustrative of configurations useful for performing spectroscopic measurements involved in the invention.

Conventional means are utilized for inducing fluorescence and detecting the induced fluorescence. For example, a photomultipler tube is utilized to indicate the presence of electromagnetic radiation. The detection means is advantageously employed in conjunction with an expedient which limits the light incident on the detector to frequencies within the monitored fluorescent band. For example, a filter or monochromator is advantageously utilized to avoid light scattered from the excitation source or to avoid radiation from the environment. Electromagnetic frequencies outside the fluorescence range should typically be limited to less than 1 percent of the detected radiation. Higher percentages, although not precluded, lead to excess uncertainty in the intensity of fluorescence. Typical configurations for monitoring are shown in FIGS. 1 and 2. In FIG. 1 an excitation wavelength is chosen utilizing a broadband light source and monochromater. The excitation is incident on the sample, 21. (This sample is shown in greater detail in FIG. 3 where 31, the material containing the fluorescing species, 32, is the enhancing surface, and 33 is the substrate.) Detection is accomplished as indicated. Alternatively, as shown in FIG. 2, exciting light, 20, is directed through a prism, 40, onto a substrate, 50, to the enhancing surface which interacts with fluorescing species in the form, for example, of a solid as shown in FIG. 3 or a liquid, 30 as shown in FIG. 2. Detection is accomplished, as discussed, and the point of the detection is not critical. Various positions such as shown in FIG. 2 are suitable. Sample preparation such as that of FIG. 3 is accomplished, for example, by spinning or by interacting the enhancing surface with a liquid having the fluorescing species.

The following example is illustrative of the subject invention.

EXAMPLE

1. Preparation of Substrates

The substrates employed were 1 inch square glass plates made by cutting standard microscope slides into 3 equal pieces. These glass plates were cleaned with a laboratory glassware detergent by rubbing with a soft brush for 30 to 60 seconds on each side. The slide was sequentially rinsed first under running hot-tap water for 20 seconds and then under deionized water for 5 seconds. The slide was blown dry with nitrogen using an air gun with a dust filter. Care was taken not to contaminate the substrates with fingerprints or other oily residues after cleaning.

2. Deposition of a Silver Film

The substrates were placed in a vacuum chamber equipped with a tungsten boat filament. A charge of silver (99.999 pure) was placed in the boat. The substrates were placed on a sample holder approximately 8 inches from the filament and were masked from it by a movable aluminum plate. Evaporation was accomplished by first pumping the chamber to a background pressure of $10^{-5}$ to $10^{-6}$ Torr. The filament was then heated by passing approximately 40 to 50 amps of current through it. The deposition rate was adjusted to a level of 2.5 to 3.0 Å/s as monitored by a Inficon Model XTM thickness monitor by adjusting the current. After the deposition rate had stabilized, the mask covering the substrates was slowly swept so as to completely expose the substrate after 75 seconds. The mask was then replaced. The filament current was eliminated and the vacuum system was backfilled with $N_2$ to atmospheric pressure. In this way, a silver film was produced that varied in thickness from approximately 200 Å at one end of the substrate to approximately 5 Å at the opposite end of the substrate.

3. Coating of Substrates

The substrates were coated with a dye solution by placing the sample on a spin coater with the metallized side exposed. Three drops of a $3 \times 10^{-5}$M rhodamine B methanol solution was placed in the center of the substrate. The substrate was spun at 7000 rpm for 30 seconds producing a uniform film thickness without reliance on the affinity of the molecule for the surface of the substrate. To introduce a quencher, appropriate volumes of a ferrous sulfate methanol solution were added to the dye solution before introduction onto the substrate.

4. Measurement of Fluorescence

The coated sample was mounted in a lens holder. The lens holder was attached to a post which was, in turn, mounted on a translation state with a 1 inch travel. The lens holder was oriented so that translation was parallel to the coated surface of the sample in the direction of the silver film thickness gradient. The sample was illuminated with light from a coherent radiation argon ion laser operating at the 514.5 nm line. The laser beam was modulated with a variable frequency chopper, passed through a 514.5 nm bandpass filter, and directed onto the dye coated surface through a slit mask placed 8 inches from the sample. The illuminated area measured 1 mm $\times$ 5 mm. The illumination was at 30 degrees to the normal.

The light from the sample was collected with a 50 mm focal length, 25 mm diameter lens oriented 45 degrees to the substrate normal. The collected light was refocused with a 200 mm focal length, 25 mm diameter lens, onto the entrance slit of a double monochromater. The lenses were translated in vertical and horizontal directions to maximize the signal. The monochromater was equipped with 1200 groove/mm holographic grating. Detection of the dispersed radiation was with a cooled RCA C31034/76 photomultiplier. The photomultiplier was biased at 1250 V with a regulated high-voltage power supply. The output of the photomultiplier was detected with a lock-in amplifier equipped with a preamplifier. The output of the lock-in amplifier was displayed on an X-Y recorder. The sensitivity settings of the amplifier and the recorder were set to yield a convenient deflection. The monochromater entrance and exit slit widths were set at 0.5 mm. The monochromater intermediate slits were set at 2.5 mm.

The ratio of the fluorescence intensity for a substrate having only the dye/quencher film compared to the fluorescence for the same film formed on the metallized substrate was determined. For an unquenched sample and for quencher concentrations in a methanol solution of 0.002 M, 0.01 M, and 0.05 M, respectively, the monitored ratio was 4.5, 22, 230, and greater than 200.

What is claimed is:

1. A process for determining the presence of a fluorescing species in a condensed phase sample that interacts with an entity that quenches said fluorescence, said process comprising the steps of exciting said fluorescing species with electromagnetic radiation and monitoring the electromagnetic radiation emanating from said sample wherein said species in said sample is allowed to interact with a Raman enhancing surface during said determination.

2. The process of claim 1 wherein said monitoring is accomplished with a photomultiplier.

3. The process of claim 1 wherein said sample is a liquid.

4. The process of claim 1 wherein said sample is a solid.

5. The process of claim 1 wherein said exciting electromagnetic radiation is coherent.

6. The process of claim 1 wherein said exciting electromagnetic radiation is incoherent.

7. The process of claim 1 wherein said Raman enhancing surface comprises a metal chosen from the group consisting of silver, copper, and gold.

* * * * *

UNITED STATES PATENT AND TRADEMARK OFFICE
CERTIFICATE OF CORRECTION

PATENT NO. : 4,549,807

DATED : October 29, 1985

INVENTOR(S) : Timothy D. Harris

It is certified that error appears in the above-identified patent and that said Letters Patent is hereby corrected as shown below:

Change the inventor's name to --Timothy D. Harris--.

Signed and Sealed this

Thirteenth Day of October, 1987

*Attest:*

DONALD J. QUIGG

*Attesting Officer*     *Commissioner of Patents and Trademarks*